(12) United States Patent
Stephan et al.

(10) Patent No.: US 7,807,615 B2
(45) Date of Patent: Oct. 5, 2010

(54) PRODUCTION OF (CO)SURFACTANTS BY REACTING POLYOLS WITH OLEFINS

(75) Inventors: Juergen Stephan, Mannheim (DE); Michael Roeper, Wachenheim (DE); Thomas Heidemann, Viernheim (DE); Michael Triller, Mannheim (DE); Juergen Tropsch, Roemerberg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 185 days.

(21) Appl. No.: 11/911,028

(22) PCT Filed: Apr. 5, 2006

(86) PCT No.: PCT/EP2006/061355

§ 371 (c)(1), (2), (4) Date: Oct. 9, 2007

(87) PCT Pub. No.: WO2006/106124

PCT Pub. Date: Oct. 12, 2006

(65) Prior Publication Data

US 2008/0176782 A1    Jul. 24, 2008

(30) Foreign Application Priority Data

Apr. 7, 2005    (DE) .................. 10 2005 016 152

(51) Int. Cl.
*C11D 1/66*    (2006.01)
(52) U.S. Cl. ...................... 510/505; 568/619
(58) Field of Classification Search ................. 568/619; 510/505
See application file for complete search history.

(56) References Cited

U.S. PATENT DOCUMENTS

| | | | |
|---|---|---|---|
| 1,968,033 A | 7/1934 | Evans et al. | |
| 2,235,785 A | 3/1941 | White | |
| 3,170,915 A | 2/1965 | Gaertner | |
| 4,404,408 A | 9/1983 | Wirth et al. | |
| 4,694,084 A | 9/1987 | Breuninger et al. | |
| 5,153,179 A | 10/1992 | Eibl | |
| 5,731,476 A * | 3/1998 | Shawl et al. | 568/619 |
| 5,741,948 A * | 4/1998 | Kirishiki et al. | 568/619 |
| 2001/0056212 A1 | 12/2001 | Okutsu et al. | |
| 2004/0186325 A1 | 9/2004 | Maas et al. | |

FOREIGN PATENT DOCUMENTS

| | | |
|---|---|---|
| DE | 40 21 511 A1 | 1/1992 |
| DE | 41 18 568 A1 | 12/1992 |
| DE | 42 22 183 A1 | 1/1994 |
| DE | 44 45 635 A1 | 6/1996 |
| DE | 195 44 413 A1 | 6/1997 |
| DE | 100 36 423 A1 | 3/2001 |
| EP | 0 649 829 A1 | 4/1995 |
| EP | 0 718 270 A2 | 6/1996 |
| EP | 0 846 671 A2 | 6/1998 |
| EP | 1 160 232 A2 | 12/2001 |
| EP | 0747 339 B2 | 7/2002 |
| EP | 0 850 907 B1 | 9/2004 |
| JP | 2001-39914 | 2/2001 |
| WO | WO 9401389 * | 1/1994 |
| WO | WO 9401389 A1 * | 1/1994 |

\* cited by examiner

*Primary Examiner*—Milton I Cano
*Assistant Examiner*—M. Reza Asdjodi
(74) *Attorney, Agent, or Firm*—Oblon, Spivak, McClelland, Maier & Neustadt, L.L.P.

(57) ABSTRACT

The present invention relates to a process for preparing polyol alkyl ethers by reacting compounds comprising at least three hydroxyl functionalities with olefins in the presence of acidic catalysts at temperatures of from 20 to 250° C. and pressures of from 0.5 to 10 bar, wherein the olefins correspond to the general formula (I)

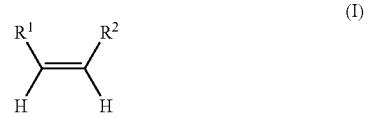

(I)

in which $R^1$ is hydrogen and $R^2$ is a linear or branched carbon radical having from 7 to 28 carbon atoms, or $R^1$ and $R^2$ are each linear or branched carbon radicals having from 1 to 27 carbon atoms, the sum of the carbon number of $R^1$ and $R^2$ being at most 28, to polyol alkyl ethers derived from compounds having at least three hydroxyl functionalities, not more than all but one hydroxyl functionality being replaced by a moiety of the general formula (VIII)

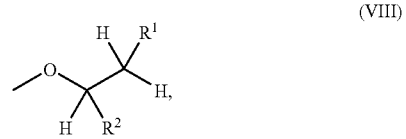

(VIII)

to the use of these polyol alkyl ethers as surfactants and to laundry detergents and cleaning compositions comprising these polyol alkyl ethers.

18 Claims, No Drawings

PRODUCTION OF (CO)SURFACTANTS BY REACTING POLYOLS WITH OLEFINS

CROSS REFERENCE TO RELATED APPLICATION

This application is a 371 of PCT/EP06/061355, filed Apr. 5, 2006, and claims priority to German Patent Application No. 10 2005 016 152.9 filed on Apr. 7, 2005.

The present invention relates to a process for preparing polyol alkyl ethers, to the thus obtained polyol alkyl ethers and to the use of these polyol alkyl ethers as surfactants, for example in laundry detergents and cleaning compositions.

To date, nonionic surfactants have usually been prepared by addition of alkylene oxides to surfactant alcohols or fatty alcohols. The surfactant alcohols required for this purpose can be obtained by Hydroformylation and subsequent hydrogenation of olefins with carbon monoxide and hydrogen. Disadvantages of this process are the high cost of reactors and safety measures, and also the generation of synthesis gas in a preceding, additional process step.

Direct oxidation of paraffins in the presence of boric acid (Bashkirov oxidation). This process gives rise to secondary alcohols which are difficult to alkoxylate. The availability of linear paraffins is not always ensured.

Ziegler process: in the so-called Alfol synthesis, the trialkylaluminum compounds prepared from ethylene and triethylaluminum are oxidized with air to the corresponding alkoxides and subsequently hydrolyzed to alcohols and $Al_2O_3$. Problems in this process are the handling of aluminum alkyl compounds and the coproduction of alumina.

Alternatively, surfactant alcohols may be prepared by the following processes:

Hydration of olefins. The preparation of surfactant alcohols by the hydration of olefins is only possible with difficulty owing to the unfavorable equilibrium position and the low reaction rate.

For the preparation of surfactants, the addition of primary alcohols to double bonds is only possible with difficulty, since nonactivated alcohols react only slowly owing to their inadequate nucleophilicity. The activation of the primary alcohols in mercuration/oxymercuration includes the disadvantage of the use of toxic mercury compounds.

The reaction of (polyalkylene)diols with olefins, preferably reaction of monoethylene glycol with olefins, is known.

For instance, EP 0 747 339 B2 discloses a process for preparing polyalkylene glycol monoalkyl ethers from olefins and (poly)alkylene glycols. In this process, olefins such as octene, decene, dodecene, tetradecene, hexadecene, octadecene are reacted with alcohols selected from monoethylene glycol, diethylene glycol, triethylene glycol, monopropylene glycol, 1,3-propanediol and others in the presence of crystalline metallosilicates as catalysts.

EP 0 846 671 A2 discloses a process for preparing (poly)alkylene glycol monoalkyl ethers by reacting olefins selected from $C_8$- to $C_{30}$-olefins which have the double bond in the α-position or in an internal position with alcohols such as monoethylene glycol, diethylene glycol, monopropylene glycol, 1,3-propanediol and others in the presence of resins, zeolites or homogeneous acidic catalysts.

EP 0 850 907 B1 discloses a process for preparing higher secondary alcohol alkoxylate compounds by reacting long-chain olefins having from 8 to 30 carbon atoms, the double bond being present in the α-position or internally, with from 1 to 50 equivalents of a $C_2$- to $C_8$-alkylene oxide.

One disadvantage of the prior art processes is that the glycols used as substrates have to be prepared in a further process step. Furthermore, the diaddition products obtained there as a by-product (dialkyl ethers) are worthless, since their hydrophilicity is insufficient for use as surfactants.

DE 195 44 413 A1 discloses a process for preparing polyol alkyl ethers by reacting compounds which have at least two hydroxyl functions, in the presence of acidic catalysts at temperatures of from 50 to 120° C. and pressures of from 50 to 30 bar, with olefins, the reaction being carried out in the liquid phase in the presence of a solvent. Short-chain olefins such as isobutene are used.

DE 44 45 635 A1 discloses a process for preparing polyol alkyl ethers in which polyhydroxyl compounds selected from the group consisting of alkylene glycols, glycerol, trimethylolpropane and pentaerythritol are reacted, in the presence of acidic catalysts at temperatures of from 50 to 120° C. and pressures of from 50 to 30 bar, with short-chain olefins such as $C_3$- to $C_6$-α-olefins or $C_4$-$C_{10}$-vinylideneolefins. To achieve a high conversion in a short reaction time, the reaction is carried out in the liquid phase in the presence of a solvent.

DE 42 22 183 A1 discloses a process for preparing polyol alkyl ethers by reacting polyhydroxyl compounds selected from the group consisting of alkylene glycols, glycerol, oligoglycerols, trimethylolpropane, pentaerythritol, 1,12-dodecanediol and sorbitol, in the presence of acidic catalysts, with short-chain $C_3$- to $C_8$-α-olefins and $C_4$- to $C_{14}$-vinylideneolefins. The catalysts used are heterogeneous catalysts such as acidic ion exchangers or zeolites, and also homogeneous acidic catalysts. DE 42 22 183 A1 further discloses the use of the polyol alkyl ethers mentioned as solvents in detergents, dyes, coatings and as fuel additives.

The processes mentioned disclose the reaction of polyhydroxyl compounds with short-chain olefins. Owing to the weak hydrophobic character of the side chains, the compounds disclosed, which stem from the reaction of short-chain olefins with polyhydroxyl compounds, are only insufficiently suitable as surfactants.

It is an object of the present invention to provide a process by which compounds which are particularly suitable as surfactants in detergents can be prepared efficiently and in one step.

This object is achieved by a process for preparing polyol alkyl ethers by reacting compounds comprising at least three hydroxyl functionalities with olefins in the presence of acidic catalysts at temperatures of from 20 to 250° C. and pressures of from 0.5 to 10 bar, wherein the olefins correspond to the general formula (I)

(I)

in which $R^1$ is hydrogen and $R^2$ is a linear or branched carbon radical having from 7 to 28 carbon atoms, or $R^1$ and $R^2$ are each linear or branched carbon radicals having from 1 to 27 carbon atoms, the sum of the carbon number of $R^1$ and $R^2$ being at most 28.

In a preferred embodiment, the compounds comprising at least three hydroxyl functions are selected from the group consisting of compounds of the general formula (II)

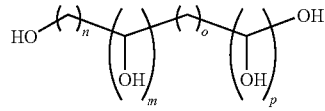
(II)

in which n=from 1 to 5, preperably from 1 to 3, m=from 1 to 10, preferably from 1 to 5, o=from 0 to 5, preferably from 0 to 3, and p=from 0 to 5, preferably from 0 to 3, compounds of the general formula (III)

(III)

in which $R^3$ is a linear or branched carbon radical having from 1 to 6 carbon atoms, preferably methyl or ethyl, q=0 or 1, r=3 or 4 and q+r=4, compounds of the general formula (IX)

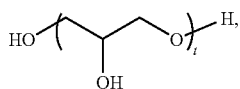
(IX)

in which t is 1 to 20, and which can be linear or branched and mixtures of the compounds of the general formulae II, III and IX.

The ether bonding in compounds of the general formula (IX) can be, as shown, constituted via primary hydroxy functionalities, so that linear compounds of the general formula (IX) are obtained. If the ether bonding in compounds of the general formula (IX) is constituted via at least one secondary hydroxy functionality, branched compounds are obtained.

In a particularly preferred embodiment, the compound comprising at least three hydroxyl functions is selected from the group consisting of glycerol, sorbitol, trimethylolpropane, pentaerythritol, compounds of the formula (IV), (V), (VI) and (IX) and mixtures thereof.

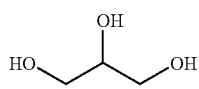
glycerol

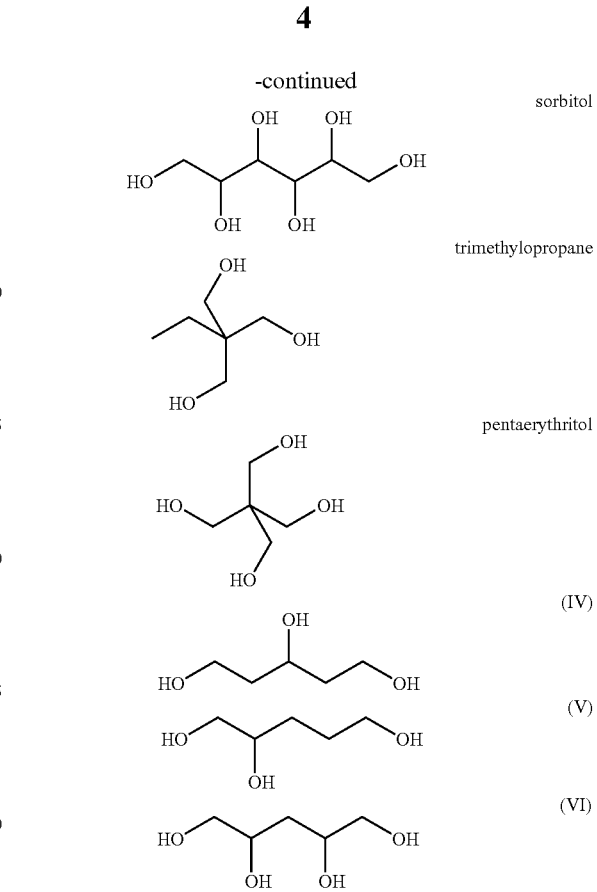

The compound is most preferably selected from a group consisting of glycerol, sorbitol, trimethylolpropane, pentaerythritol and mixtures thereof.

The compounds comprising at least three hydroxyl functions may be prepared or obtained by processes known to those skilled in the art.

Natural glycerol is obtained on a large scale as a by-product in the hydrolysis, saponification or transesterification of fats. In this context, mention should be made in particular of the production of "biodiesel", which is constantly increasing worldwide, in which triglycerides (fats, oils) are reacted with methanol to give the corresponding fatty acid methyl esters and the glycerol which occurs as a coupling product.

Synthetic glycerol can be prepared via the following routes which start from propene:

Routes for Synthesis of Glycerine from Propylene

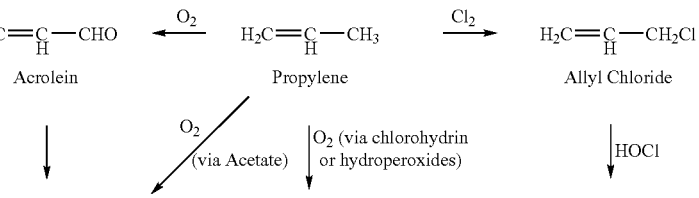

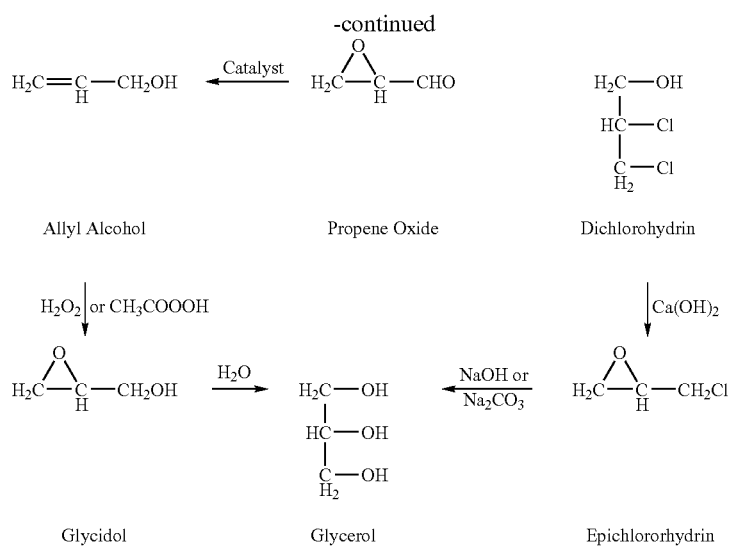

Sorbitol is obtained by nickel- or rhodium-catalyzed hydrogenation of glucose.

Pentaerythritol is prepared by condensation of formaldehyde and acetaldehyde in the presence of a base. The pentaerythrose formed reacts by Cannizaro reaction to give pentaerythritol and sodium formate.

Trimethylolpropane is prepared by condensation of formaldehyde and butyraldehyde in the presence of a base; the 2,2-dimethylolbutyraldehyde formed is reacted in a Cannizaro reaction with formaldehyde in the presence of NaOH to give trimethylolpropane.

Diglycerine, t=2 in formula (IX), kann be prepared by heating of gylcerine to 290-295° C. according to DE 181754, by heating of glycerine with earthalkali hydroxides or sodium silicate, as described in DE 494430 and DE 494431 or by basic hydrolysis of epichlorohydrine.

Polyglycerines of the general formula (IX) can be obtained by heating of glycerine with alkali according to DE 198768 or U.S. Pat. No. 3,637,774, by reaction of Isopropylideneglycerine with α-monochlorohydrine (basic) and subsequent hydolysis according to U.S. Pat. No. 5,243,086 or DE 4132171, by heating of glycerine with glycerine carbonate catalysed by a base or an acid according to JP 100772392 or heterogeneously catalysed according to JP 10072393, by heating of glycerine with epichlorohydrine catalysed by a base according to U.S. Pat. No. 4,960,953, or by reaction of glycidol with glycerine according to A. Kleemann, R. Wagner, Hüthig-Verlag, Heidelberg, 1981, 62-63.

The olefins used in the process according to the invention correspond to the general formula (I)

(I)

in which $R^1$ is hydrogen and $R^2$ is a linear or branched carbon radical having from 7 to 28 carbon atoms, or $R^1$ and $R^2$ are each linear or branched carbon radicals having from 1 to 27 carbon atoms, the sum of the carbon atoms of $R^1$ and $R^2$ being at most 28.

The olefins which are described by the general formula (I) are α-olefins having from 9 to 30 carbon atoms, or olefins which have from 4 to 30 carbon atoms and have the double bond in an internal position.

Suitable processes for preparing the olefins which can be used in accordance with the invention are known to those skilled in the art.

α-Olefins having a chain length of at least 9 carbon atoms are prepared virtually exclusively by separating the α-olefin with the desired chain length from mixtures prepared by oligomerization of ethene (what is known as a full-range process in contrast to on-purpose processes). To this end, for example, the processes of Chevron Philipps (use of an $AlEt_3$ catalyst in dilute solution), of BP (concentrated $AlEt_3$ solution), of Idemitsu (use of an Al/Zr complex) or of Shell (ligand-modified nickel system) are known. In the Shell process, there is additionally also a sequence of isomerization and subsequent metathesis reaction of the olefins in order thus to obtain internal olefins. The internal olefins obtained in this way are likewise suitable for the inventive use.

New full-range processes are, for example, the AlphaSelect® process of Axens or the Alpha-Sablin® process of Linde/Sabic, which use catalysts based on zirconium/aluminum. Mention should also be made of the process of UOP/Dow (Linear-1®).

On-purpose processes for α-olefins having more than 8 carbon atoms have to date not been implemented industrially. There exist applications of BASF Aktiengesellschaft for a process for preparing 1-decene (EP 10103309, EP 10128048).

It is additionally possible to use: (linear) internal olefins from the SHOP process or else branched olefins. These are obtained, for example, by trimerization of n-butenes (EP 1030825) or else dimerization of hexenes, as described in EP 1268370 (BASF Aktiengesellschaft), WO 00/69795 (BASF Aktiengesellschaft) or EP 1159236.

In a preferred embodiment, olefins selected from the group consisting of internal, branched olefins of chain length $C_{12}$, linear or branched, preferably linear, α-olefins of chain length $C_{12}$ and $C_{14}$, 1-dodecene and/or 1-tetradecene, and mixtures thereof, are used in the process according to the invention.

In a particularly preferred embodiment, a $C_{12}$-α-olefin, a $C_{14}$-α-olefin or a mixture of a $C_{12}$- and of a $C_{14}$-α-olefin is used. A preferred mixture of $C_{12}$-, $C_{14}$-α-olefins contains 95% by weight α-olefins, being 67±3% by weight 1-dodecene and 1-tetradecene.

Internal, branched olefins of chain length $C_{12}$ can be prepared by dimerizing hexenes, as described in EP 1268370 (BASF Aktiengesellschaft), WO 00/69795 (BASF Aktiengesellschaft), EP 1159236 (BASF Aktiengesellschaft), or by trimerizing butenes as described in EP 1030825.

In a further preferred embodiment, an internal, lightly branched olefin mixture with the following composition is used:
10-18% by weight of olefin derived from n-dodecane,
25-40% by weight of olefin derived from 5-methyl-n-undecane,
25-40% by weight of olefin derived from 4-ethyl-n-decane,
2-8% by weight of olefin derived from 5,6-dimethyl-n-decane,
5-12% by weight of olefin derived from 5-ethyl-6-methyl-n-nonane,
1-5% by weight of olefin derived from 4,5-diethyl-n-octane
and at most 5% by weight of other hydrocarbons.

The process according to the invention is carried out in the presence of acidic catalysts. The acidic catalysts may be present in heterogeneous or homogeneous form in the reaction mixture, preference being given to heterogeneous catalysts.

Suitable homogeneous catalysts are strong acids, for example alkylsulfuric acids, para-toluenesulfonic acids, generally alkyl- and arylsulfonic acids, phosphoric acid, trifluoromethanesulfonic acid, HF, $SO_3$, boric acid, perchloric acid or Lewis acids, for example $BF_3$, $BCl_3$, $AlBr_3$, $FeCl_3$, $SnCl_4$, $SbCl_5$, $AsF_5$, $AsF_3$, $TiCl_4$, $AlMe_3$ or related compounds.

Suitable heterogeneous catalysts for the present process are strong acids such as ion exchangers based on divinylbenzene with sulfonic acid groups (for example Amberlyst 15 from Rohm & Haas), heteropolyacids and salts thereof (for example $H_4SiMo_{12}O_{40}$, $H_3PMo_{12}O_{40}$, $H_3PW_{12}O_{40}$) on support materials such as $SiO_2$, $Al_2O_3$, $TiO_2$, $ZrO_2$, etc, and also acidic mixed oxides (for example $WO_3/TiO_2$).

Also suitable are porous metallosilicates, especially aluminosilicates. This comprises mesoporous aluminosilicates such as MCM-41, SBA-15, MSU-S, MAS-5, MAS-7, MAS-9. These materials are described in "Catalysis Surveys from Asia", 2004, Vol. 8, No. 3, p.151 ff., and the references present therein. Particularly suitable are crystalline metallosilicates such as aluminosilicates, ferrosilicates, borosilicates or gallosilicates.

In a preferred embodiment, the acidic catalyst used is a zeolite.

Examples of zeolites which may be used in accordance with the invention are zeolites of the structure types FER (e.g. ferrierite), MFI and MEL (pentasils, e.g. ZSM-5, ZSM-11), FAU (e.g. X, Y, USY), LTL (Linde type L), MOR (mordenite), BEA (β-zeolite), MTW (e.g. ZSM-12), GME (e.g. gmelinite), MAZ (mazzite) and MWW (e.g. MCM-22). Owing to their advantageous catalytic properties, preference is given among this group to BEA, MFI, MEL MOR, FAU and MWW zeolites. Very particular preference is given to BEA zeolites.

These zeolites are preferably used in their H form, but metal ions from groups IA and IIA of the periodic table of the elements (CAS nomenclature) and also Ti, Cr, Mn, Fe, Ni, Cu, Co, Ag, Zn or La may also be present in nonlattice positions. The metal ions may be incorporated during the zeolite synthesis or afterward by metal ion exchange or by impregnation.

The catalyst may be used directly as a fine powder in suspension; in the case of zeolites, these are generally particle sizes between 100 nm and a few μm.

However, these catalysts may equally be shaped together with binder materials to give moldings. Suitable binders are particularly clays, aluminas, for example Pural, and silicas, for example Silres. Suitable moldings are tablets, strand extrudates, rings, ribbed extrudates, star or wagon wheel extrudates. Usual diameters are 0.1-5 mm.

The catalysts have specific surface areas of from 30 to 2000 $m^2/g$, preferably from 100 to 900 $m^2/g$. The volume of the pores of diameter 2-20 nm is typically 0.05-0.5 ml/g, preferably 0.1-0.3 ml/g, that of the pores of 20-200 nm typically from 0.005 to 0.2 ml/g, preferably from 0.01 to 0.1 ml/g and that of the pores of 200-2000 nm typically 0.05-0.5 ml/g, preferably from 0.05 to 0.3 ml/g.

Deactivated catalysts may be reactivated, for example, by burning-off in air or lean air at 250-550° C. Alternatively to burning-off, a treatment with at lower temperature, either in the liquid or in the gas phase, with mineral acids, for example sulfuric acid or hydrochloric acid, with organic solvents or with oxidizing compounds is possible; mention should be made here in particular of $NO_x$, $H_2O_2$ and their halogens. The regeneration may be effected directly in the reactor or externally.

The catalysts which can be used in accordance with the invention are commercially available or can be prepared by methods known to those skilled in the art.

The process is carried out at a temperature of from 20 to 250° C., preferably from 40 to 200° C., more preferably from 80 to 180° C.

The process according to the invention is carried out at a pressure of from 0.5 to 10 bar, preferably from 0.6 to 5 bar, more preferably at atmospheric pressure.

The process according to the invention may be carried out in the presence or in the absence of a solvent. In a preferred embodiment, the process according to the invention is carried out in the presence of a solvent.

Suitable solvents are monohydric alcohols having from 1 to 6 carbon atoms, low molecular weight ethers, aromatic compounds such as benzene or toluene, chlorinated solvents such as methylene chloride, chloroform or carbon tetrachloride, 1,4-dioxane, 1,3-dioxane, sulfolane, THF or compounds of the general formula (VII)

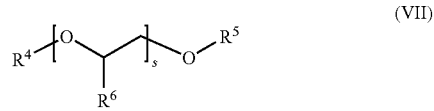

(VII)

in which $R^4$, $R^5$ and $R^6$ are each independently hydrogen, $C_1$-$C_{10}$-alkyl, -alkenyl or -alkynyl; $R^4$ and $R^5$ are preferably $C_1$-$C_3$-alkyl; $R^6$ is further preferably hydrogen or methyl, more preferably hydrogen; s is an integer from 1 to 5, preferably from 2 to 4. It is also possible to use mixtures of the solvents mentioned. For the reaction of solid polyol components, such as sorbitol, it is also possible, for example, to use glycerol as the solvent, which leads to product mixtures. Additionally suitable for sorbitol are polar solvents, for example DMSO or acetonitrile.

Preference is given to using 1,4-dioxane, 1,3-dioxane, diglyme, triglyme or mixtures thereof as solvents. It is also possible to use mixtures of the solvents mentioned.

In a preferred embodiment, the process according to the invention is carried out in an inert atmosphere. The inert gases used may be nitrogen and/or noble gases, preferably helium and/or argon. Preference is given to using an inert atmosphere consisting of nitrogen.

Useful reaction vessels for the process according to the invention are all vessels known to those skilled in the art, for example continuous, semicontinuous or batchwise glass or metal stirred tanks or pressure autoclaves.

The process according to the invention may be carried out either continuously or batchwise. In continuous mode, the substrates are fed continuously to the reactor, and the products are removed continuously from the reactor, so that the concentrations of the individual components in the reactor remain constant.

The reaction product can be worked up and/or purified by the process known to those skilled in the art. For workup, the phase comprising the product may be removed by decanting-off or by means of a separating funnel. Moreover, the product can also be removed by distillation. The product can also be purified by distillation. Unconverted substrates can be reused in the reaction after they have been removed.

The present invention also relates to polyol alkyl ethers preparable by the process according to the invention.

The present invention further relates to polyol alkyl ethers derived from compounds having at least three hydroxyl functionalities, not more than all but one hydroxyl functionality being replaced by a moiety of the general formula (VIII)

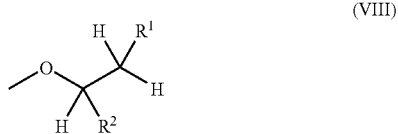

(VIII)

and the $R^1$ and $R^2$ radicals are each as defined in the compounds of the general formula (I).

The moiety of the general formula (VIII) derives from the olefins of the general formula (I).

In a preferred embodiment, the moiety of the general formula (VIII) derives from olefins selected from the group consisting of internal, branched olefins of chain length $C_{12}$, linear or branched, preferably linear, α-olefins of chain length $C_{12}$ and $C_{14}$, 1-dodecene and/or 1-tetradecene, and mixtures thereof.

In a particularly preferred embodiment, the moiety of the general formula derives from $C_{12}$-α-olefins, $C_{14}$-α-olefins or from a mixture of a $C_{12}$- and of a $C_{14}$-α-olefin.

In a preferred embodiment, the polyol alkyl ethers are derived from compounds having at least three hydroxyl functionalities, selected from the group consisting of glycerol, sorbitol, trimethylolpropane, Pentaerythritol, compounds of the general formula (IX) and mixtures thereof.

The present invention also relates to laundry detergents and cleaning compositions which comprise the inventive polyol alkyl ethers.

These laundry detergents and cleaning compositions may be in powder, granule, extrudate or tablet form.

In laundry detergents, the inventive polyol alkyl ethers may be combined with the customary additives known to a person skilled in the art in amounts of from 0.1 to 40% by weight, preferably from 0.5 to 30% by weight, more preferably from 1 to 20% by weight. Examples of suitable additives comprise:

builders and cobuilders, for example polyphosphates, zeolites, polycarboxylates, phosphonates, citrates, complexing agents, ionic surfactants, for example alkylbenzenesulfonates, α-olefinsulfonates and other alcohol sulfates/ether sulfates, other nonionic surfactants, for example alkylamino alkoxylates and alkylpolyglycosides, amphoteric surfactants, for example alkylamine oxides, betaines, optical brighteners, dye transfer inhibitors, for example polyvinylpyrrolidone, standardizers, for example sodium sulfate, magnesium sulfate, soil release agents, for example polyethers/polyesters, carboxymethylcellulose, encrustation inhibitors, for example polyacrylates, copolymers of acrylic acid and maleic acid, bleach systems consisting of bleaches, for example perborate or percarbonate, plus bleach activators, for example tetraacetylethylenediamine, plus bleach stabilizers, perfume, foam inhibitors, for example silicone oils, alcohol propoxylates (in particular in liquid laundry detergents), enzymes, for example amylases, lipases, proteases or carbonylases, alkali donors, for example pentasodium metasilicate or sodium carbonate.

Further constituents known to those skilled in the art may likewise be present.

In the conventional form, the pulverulent laundry detergents have an average bulk density of approx. 450 g/l. Compact or ultracompact laundry detergents have a bulk density of >600 g/l.

Liquid laundry detergents may additionally comprise solvents, for example ethanol, isopropanol, 1,2-propylene glycol or butylene glycol.

Gel-form laundry detergents additionally comprise thickeners, for example polysaccharides and lightly crosslinked polycarboxylates, for example the Carbopol® brands from BF Goodrich.

In tablet-form laundry detergents, further additives are required. These are, for example, tableting assistants, for example polyethylene glycols with molar masses of >1000 g/mol or polymer dispersions. Also required are tablet disintegrants, for example cellulose derivatives, crosslinked polyvinylpyrrolidone, crosslinked polyacrylates or combinations of acids, for example citric acid, with sodium carbonate.

In detergents for hard surfaces, for example acidic detergents, alkaline detergents, neutral detergents, machine dishwashing, for metal degreasing, glass detergents, floor detergents, the inventive polyol alkyl ethers are combined with the additives which are listed below and are present in amounts of from 0.01 to 40% by weight, preferably from 0.1 to 20% by weight:

ionic surfactants, for example alkylbenzenesulfonates, α-olefinsulfonates, other alcohol sulfonates/ethersulfonates, sulfosuccinates, other nonionic surfactants, for example alkylamine alkoxylates and alkylpolyglucosides, amphoteric surfactants, for example alkylamine oxides, betaines, builders, for example polyphosphonates, polycarboxylates, phosphonates, complexing agents, dispersants, for example naphthalenesulfonic acid condensates, polycarboxylates, pH-regulating compounds, for example alkalis such as NaOH, KOH or pentasodium metalsilicate or acids, for instance hydrochloric acid, phosphoric acid, aminosulfuric acid, citric acid, enzymes, for example lipases, amylases, proteases, carboxylases, perfumes, dyes, biocides, for example isothiazolinones, 2-bromo-2-nitro-1,3-propanediol, bleach systems consisting of bleaches, for example perborate, percarbonate, plus bleach activators, for example tetraacetylethylenediamine, plus bleach activators, solubilizers, for example cumenesulfonates, toluenesulfonates, short-chain fatty acids, alkyl/aryl phosphates, solvents, for example short-chain alkyl oligoglycols, alcohols, for example ethanol or propanol, aromatic solvents, for example toluene or xylene, N-alkylpyrrolidones, alkylene carbonates, thickeners, for example polysaccharides and lightly crosslinked polycarboxylates, for example Carbopol® brands from BF Goodrich.

These detergents for hard surfaces are usually, but not exclusively, aqueous and are in the form of microemulsions, emulsions or in solution.

Should they be in solid form, standardizers as described above may additionally be used.

In tablet-form detergents, further additives are required. These are, for example, tableting assistants, for example polyethylene glycols having molar masses of >1000 g/mol or polymer dispersions. Also required are tablet disintegrants, for example cellulose derivatives, crosslinked polyvinylpyrrolidone, crosslinked polyacrylates or combinations of acids, for example citric acid, with sodium carbonate.

The present invention also relates to the use of the inventive polyol alkyl ethers as surfactants. The inventive polyol alkyl ethers may also be used as cosurfactants in a mixture with other surfactants.

In addition to the use of the polyol alkyl ethers as surfactants in the abovementioned laundry detergents and cleaning compositions, they may also be used advantageously for a multitude of other chemical and industrial processes.

In a preferred embodiment, the inventive polyol alkyl ethers may be used as surfactants in laundry detergents and cleaning compositions, in the metal processing industry, in the production and processing of textiles, in the leather industry, paper industry, printing industry, electroplating industry and photographic industry, in water treatment, in crop protection formulations or in the plastics production industry and plastics processing industry.

The use of the inventive polyol alkyl ethers in the metal processing industry comprises, for example, use in cooling lubricants, hardening oils, hydraulic oil emulsions, polishing pastes, mold release agents, drawing oils, pickling media, metal cleaners, metal dryers.

In this context, the surfactants can be used advantageously specifically in the processes in which high thermal stability is important.

The surfactants may also be used in the production and processing of textiles. The use of surfactants in the production and processing of textiles is extremely wide, and extends mainly to the fields of pretreatment compositions of fibers, production of rayon fibers, spin preparations and textile melts, dyeing assistants, softeners, hydrophobizing agents, assistants for printing, antistats, flocking and coating compositions.

The surfactants may also be used in the leather, paper, printing, electroplating and photographic industries. Important fields of use in this context are coatings, pigments and printing inks. Surfactants are used in these fields both in aqueous and in nonaqueous systems. In nonaqueous systems, they serve in particular as dispersing assistants, antisettling agents or processing assistants. In addition, surfactants enable the production of high-solids systems in which, in addition to the stabilization of the binders which are based on polymer dispersions and are prepared by emulsion polymerization or polycondensation, they also serve as dispersing assistants of organic and inorganic pigments which are often used. In addition, they improve the adhesion properties of these coatings.

The surfactants may also be used in water treatment, for example in wastewater treatment.

The surfactants may also be used in crop protection formulations.

The polyol alkyl ethers may also be used as surfactants or emulsifiers in the plastics production and plastics processing industries. Main fields of use in plastics production and processing are production of polymer dispersions, production of bead polymers, production of foams, use of interface-active mold release agents, production of microcapsules, improvement in the adhesion between fillers and polymers, additives to polymer dispersions for achieving particular effects such as foamability, filler compatibility or wetting capacity, emulsifiers for nonaqueous systems, dyeing of polymers, antistatic modification of polymers, adhesives.

EXAMPLES

Example 1

6.6 g (0.36 mol) of 1-dodecene and 33.15 g (0.24 mol) of glycerol are weighed under a nitrogen atmosphere in a 250 ml glass flask. 2.2 g of catalyst (β-zeolite from PQ) are added to this reaction mixture. By means of a precision stirrer, the reaction mixture is stirred highly vigorously at 150° C. for three hours. The phases are separated in a separating funnel. The product is obtained from the olefinic phase by distilling off the unconverted olefin; both unconverted olefin and unconverted glycerol can be recycled into the reaction.

Example 2

64.3 g diglycerine (99%) (0.39 mol) and 64.3 g diglyme are weighed in a 250 ml glass flask under a nitrogen atmosphere and heated to 100° C. Under a countercurrent of nitrogen 13 g 1-dodecene (0.08 mol) and 1.9 g catalyst (β-zeolite from Zeolist) are added. By means of a precision stirrer, the reaction mixture is stirred highly vigorously at 150° C. for six hours. The phases are separated in a separating funnel. The product is obtained from the olefinic phase by distilling off the unconverted olefin; both unconverted olefin and unconverted glycerol can be recycled into the reaction.

Example 3

Polyglycerol-3 is prepared by heating a mixture of glycerin (99,5%) and NaOH (100%) to a temperature of 230° C. Reaction water is removed continuously. The reaction is stopped by rapid cooling to 80° C., when the desired hydroxy number (1169) is reached. Subsequently, polyglycerol-3 is dilluted with water and is neutralized by ion exchanger. Water is removed after addition of toluene with a water separator.

17,1 g 1-dodecene (0.104 mol), 52.0 g polyglycerol-3 (0.217 mol at an average molecular weight of 240 g/mol) and 104 g 1,4-dioxane are weighed into a stirring autoclave under nitrogen. 1.26 g catalyst (β-Zeolith by Zeolyst) are added and the mixture is heated to 150° C. Over a period of 24 hours the reaction mixture is stirred highly vigorously at this temperature. The phases are separated in a separating funnel after cooling. The addition product that is present in the upper organic phase is separated from that phase via destillative removing of the solvent and the unreacted olefin and can be purified, if necessary, by aqueous extraction of remainder of polyglycerole.

What is claimed is:

1. A process for preparing polyol alkyl ethers by reacting compounds comprising at least three hydroxyl functionalities with olefins in the presence of acidic catalysts at temperatures of from 20 to 250° C. and pressures of from 0.5 to 10 bar, wherein olefins selected from the group consisting of internal, branched olefins of chain length $C_{12}$, linear or branched α-olefins of chain length $C_{12}$ and $C_{14}$, and mixtures thereof are present, and wherein the compounds comprising at least three hydroxyl functionalities are selected from the group consisting of sorbitol, trimethylolpropane, pentaerythritol, compounds of formula (IV), (V), (VI), (IX) and mixtures thereof

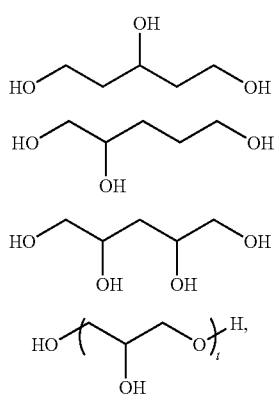

in which t is 1 to 20, and which can be linear or branched.

2. The process according to claim 1, which is carried out in the presence of a solvent.

3. The process according to claim 1, wherein a $C_{12}$-α-olefin, a $C_{14}$-α-olefin or a mixture of a $C_{12}$- and of a $C_{14}$-α-olefin is used.

4. The process according to claim 1, wherein the acidic catalyst is a zeolite.

5. A polyol alkyl ether derived from compounds having at least three hydroxyl functionalities selected from compounds of formula (IV), (V), (VI), (IX) and mixtures thereof

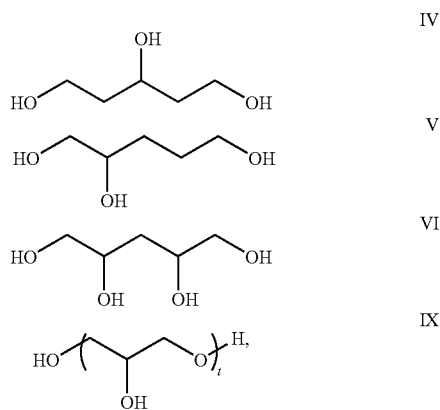

in which t is 2 to 20, and which can be linear or branched, not more than all but one hydroxyl functionality being replaced by a moiety of the general formula (VIII)

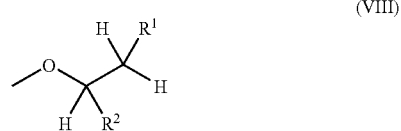

which is derived from olefins selected from the group consisting of internal, branched olefins of chain length $C_{12}$, linear or branched α-olefins of chain length $C_{12}$ and $C_{14}$, and mixtures thereof.

6. A laundry detergent or cleaning composition, which comprises polyol alkyl ethers of claim 5.

7. A method of preparing laundry detergents and cleaning compositions, in the metal processing industry, in the production and processing of textiles, in the leather industry, paper industry, printing industry, electroplating industry and photographic industry, in water treatment, in crop protection formulations or in the plastics production industry and plastics processing industry comprising adding polyol alkyl ethers derived from compounds having at least three hydroxyl functionalities, not more than all but one hydroxyl functionality being replaced by a moiety of the general formula (VIII)

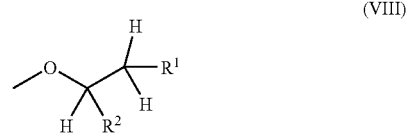

which is derived from olefins selected from the group consisting of internal, branched olefins of chain length $C_{12}$, linear or branched α-olefins of chain length $C_{12}$ and $C_{14}$, and mixtures thereof wherein the compounds comprising at least three hydroxyl functionalities are selected from the group consisting of sorbitol, trimethylolpropane, pentaerythritol, compounds of the general formula (IV), (V), (VI), (IX) and mixtures thereof

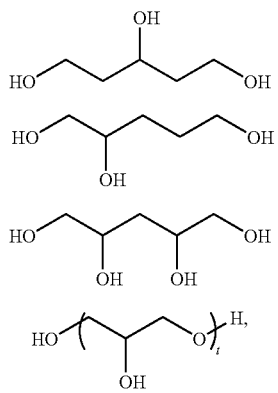

in which t is 2 to 20 and compounds of formula (IX) can be linear or branched, as surfactants to said detergents and cleaning compositions.

8. A process for preparing polyol alkyl ethers, comprising:
reacting at least one compound comprising at least three hydroxyl functionalities with at least one olefin in the presence of at least one acidic catalyst at a temperature of from 20 to 250° C. and at a pressure of from 0.5 to 10 bar, wherein said at least one olefin is selected from the group consisting of a $C_{12}\alpha$-olefin, a $C_{14}\alpha$-olefin, and a mixture thereof, and
wherein said at least one compound comprising at least three hydroxyl functionalities is selected from the group consisting of sorbitol; trimethylolpropane; pentaerythritol; a compound represented by formula (IV); a compound represented by formula (V); a compound represented by formula (VI); a compound represented by formula (IX); and a mixture thereof

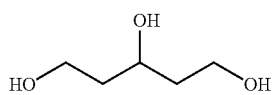

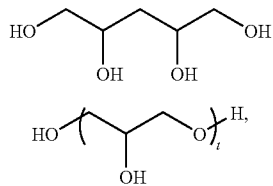

in which t is 1 to 20, and which can be linear or branched.

9. The process according to claim 8, wherein a molar ratio of the C═C moiety of said at least one olefin to the hydroxyl functionalities of said at least one compound comprising at least three hydroxyl functionalities is from 1:19.5 to 1:2.

10. The process according to claim 8, wherein said at least one acidic catalyst is a zeolite.

11. The process according to claim 10, wherein said zeolite is a BEA zeolite, a MFI zeolite, a MEL zeolite, a MOR zeolite, a FAU zeolite, or a MWW zeolite.

12. The process according to claim 8, wherein said at least one olefin is at least one of 1-dodecene and 1-tetradecene.

13. The process according to claim 8, wherein said temperature is from 80 to 180° C.

14. The process according to claim 8, wherein said pressure is from 0.6 to 5 bar.

15. The process according to claim 8, which is carried out in the presence of at least one inert gas selected from the group consisting of nitrogen, helium, and argon.

16. The process according to claim 8, which is carried out in the presence of at least one solvent selected from the group consisting of 1,4-dioxane; 1,3-dioxane; diglyme; and triglyme.

17. The process according to claim 8, wherein said at least one olefin is a mixture comprising 95% by weight of a-olefins, where 1-dodecene and 1-tetradecene make up 67±3% by weight of said mixture.

18. A laundry detergent or cleaning composition, which comprises a polyol alkyl ether of claim 8.

* * * * *